(12) United States Patent
Freeberg

(10) Patent No.: US 7,418,296 B2
(45) Date of Patent: Aug. 26, 2008

(54) WIRELESS PACING SYSTEM ANALYZER IN A PROGRAMMER SYSTEM

(75) Inventor: Scott Freeberg, Birchwood Village, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 117 days.

(21) Appl. No.: 10/903,465

(22) Filed: Jul. 30, 2004

(65) Prior Publication Data

US 2006/0025830 A1 Feb. 2, 2006

(51) Int. Cl.
*A61N 1/00* (2006.01)

(52) U.S. Cl. .............................. 607/60; 607/30; 607/32; 607/63; 128/903; 128/908

(58) Field of Classification Search .................. 607/27, 607/30, 32, 33, 60, 61, 63; 128/903, 908
See application file for complete search history.

(56) References Cited

U.S. PATENT DOCUMENTS

| | | | |
|---|---|---|---|
| 4,266,551 A | 5/1981 | Stein | |
| 4,556,063 A | 12/1985 | Thompson et al. | |
| 4,809,697 A | 3/1989 | Causey, III et al. | |
| 4,825,869 A | 5/1989 | Sasmor et al. | |
| 5,113,869 A | 5/1992 | Nappholz et al. | |
| 5,421,830 A | 6/1995 | Epstein et al. | |
| 5,458,623 A | 10/1995 | Lu et al. | |
| 5,474,574 A | 12/1995 | Payne et al. | |
| 5,509,927 A | 4/1996 | Epstein et al. | |
| 5,549,654 A | 8/1996 | Powell | |
| 5,592,512 A | 1/1997 | Spiess | |
| 5,626,630 A | 5/1997 | Markowitz et al. | |
| 5,722,999 A | 3/1998 | Snell | |
| 5,724,985 A * | 3/1998 | Snell et al. | ................... 600/510 |
| 5,807,397 A | 9/1998 | Barreras | |
| 5,974,341 A | 10/1999 | Er et al. | |
| 6,250,309 B1 | 6/2001 | Krichen et al. | |
| 6,263,245 B1 | 7/2001 | Snell | |
| 6,363,282 B1 | 3/2002 | Nicholas et al. | |
| 6,442,432 B2 | 8/2002 | Lee | |
| 6,443,890 B1 | 9/2002 | Schulze et al. | |
| 6,480,745 B2 | 11/2002 | Nelson et al. | |
| 6,497,655 B1 | 12/2002 | Linberg et al. | |
| 6,574,510 B2 | 6/2003 | Von Arx et al. | |
| 6,580,948 B2 | 6/2003 | Haupert et al. | |
| 6,602,191 B2 | 8/2003 | Quy | |
| 6,622,045 B2 | 9/2003 | Snell et al. | |
| 6,648,823 B2 | 11/2003 | Thompson et al. | |
| 6,650,944 B2 | 11/2003 | Goedeke et al. | |
| 6,669,631 B2 | 12/2003 | Norris et al. | |
| 2003/0088290 A1 | 5/2003 | Spinelli et al. | |
| 2004/0116981 A1* | 6/2004 | Mazar | .......................... 607/60 |
| 2007/0049992 A1 | 3/2007 | Freeberg | |

* cited by examiner

*Primary Examiner*—Carl H. Layno
*Assistant Examiner*—Yun Haeng Lee
(74) *Attorney, Agent, or Firm*—Schwegman, Lundberg & Woessner, P.A.

(57) ABSTRACT

An external interface device provides telemetry between an implantable apparatus and a remote device. The interface device includes a battery powered circuit and a wireless transceiver. A power supply of the remote device is isolated from the implantable apparatus by a wireless communication link.

24 Claims, 4 Drawing Sheets

WIRELESS PACING SYSTEM ANALYZER IN A PROGRAMMER SYSTEM

TECHNICAL FIELD

This document pertains generally to implantable devices, and more particularly, but not by way of limitation, to isolation for a pacing systems analyzer in a programmer system.

BACKGROUND

Programmers and other remote devices are typically used by physicians for telemetry with an implantable device. Telemetry allows testing, programming and interrogation of an implantable device. Such remote devices include safety mechanisms to assure that the patient is protected from exposure to hazardous electrical levels. Safety standards for a remote device that is to be connected with an implantable device typically include specifications for voltage isolation and current leakage.

The financial costs associated with providing medical grade electrical isolation systems in a programmer are burdensome. In addition, failures of electrical isolation can lead to severe injury or death.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed herein.

DETAILED DESCRIPTION

Figure 1A:
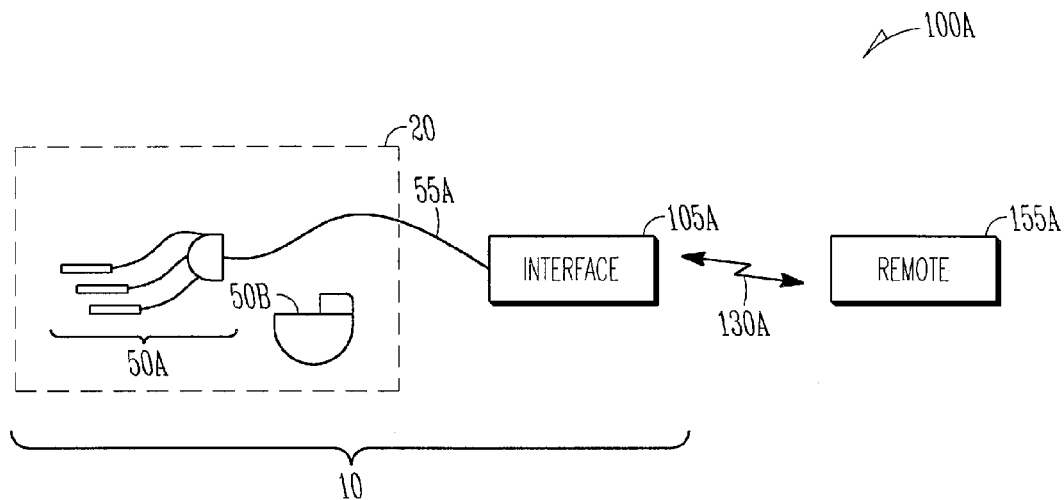
FIGS. 1A and 1B include block diagrams of telemetry systems.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The examples may be combined, other examples may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In one example, an external interface device is coupled to an implantable apparatus by a wired connection. The interface device is non-implantable and, in one example, includes a battery powered wireless transceiver. A wireless communication link between the interface device and an external programmer allows telemetry with the implantable apparatus.

The term implantable apparatus includes any implantable component (including an implantable lead or electrode and an implantable connector block) as well as an implantable device. An implantable device, in various examples, includes a therapy circuit or a monitor circuit. Exemplary therapy circuits include a pulse generator (such as a pacemaker, a cardiac rhythm therapy device, a heart failure or cardiac resynchronization device, a cardioverter/defibrillator, a pacer/defibrillator) and a drug delivery device (such as an implantable drug pump). In one example, an implantable device includes a processor and one or more telemetry systems. Examples of telemetry systems include near field telemetry (such as an inductive telemetry) and far field telemetry (such as far field radio frequency telemetry). In various examples, each telemetry system includes at least one of a receiver, a transmitter and a combined receiver/transmitter sometimes referred to as a transceiver. A power supply for an implantable device, in one example, includes a battery.

An example of a remote device, sometimes referred to as a programmer, includes a keyboard and a display. The remote device is powered by a battery or a connection to a metered line service sometimes referred to as AC mains. In one example, the power supply of the remote device complies with medical standards for isolation and safety.

FIG. 1A illustrates telemetry system 100A including implantable apparatus 50A, interface 105A and remote 155A. Electrical signals between implantable apparatus 50A and interface 105A are conducted by link 55A. Link 130A allows wireless communication between interface 105A and remote 155A, thus eliminating a corded connection between interface 105A and remote 155A.

At the time of implantation, sterile field 10 is maintained around body 20. Interface 105A, in one example, is positioned within sterile field 10 which extends some distance beyond body 20 and wireless link 130A provides a coupling to remote 155A positioned beyond sterile field 10. Interface 105A is sometimes referred to as a pacing system analyzer or PSA. Interface 105A is non-implantable.

Link 55A is illustrated as a connection between implantable apparatus 50A and interface 105A. In the figure, implantable apparatus 50A includes a connector block coupled to an electrode set. Implantable apparatus 50B, shown implanted in body 20, represents an implantable device. The figure illustrates link 55A coupled to implantable apparatus 50A, however, at another time, link 55A is coupled to implantable apparatus 50B or coupled to both implantable apparatus 50A and implantable apparatus 50B.

Remote 155A, in one example, includes a programmer for use by a physician or other medical personnel at the time of implantation as well as during follow-up visits. In various examples, remote 155A allows interrogation as well as programming of implantable apparatus 50A, and accordingly, includes a user-accessible interface such as a touch-sensitive display screen. Remote 155A, in one example, includes a remote interrogation device (sometimes referred to as a repeater) which allows connecting with a bi-directional communication network such as a local area network (Ethernet), a wide area network (such as the Internet) or telephone lines in a home (plain old telephone service via the public switched telephone network). In various examples, remote 155A includes a display monitor, a printer, a keyboard, a touch-sensitive screen, a cursor control, a speaker, a microphone, a storage device and a network interface device.

Figure 1B:
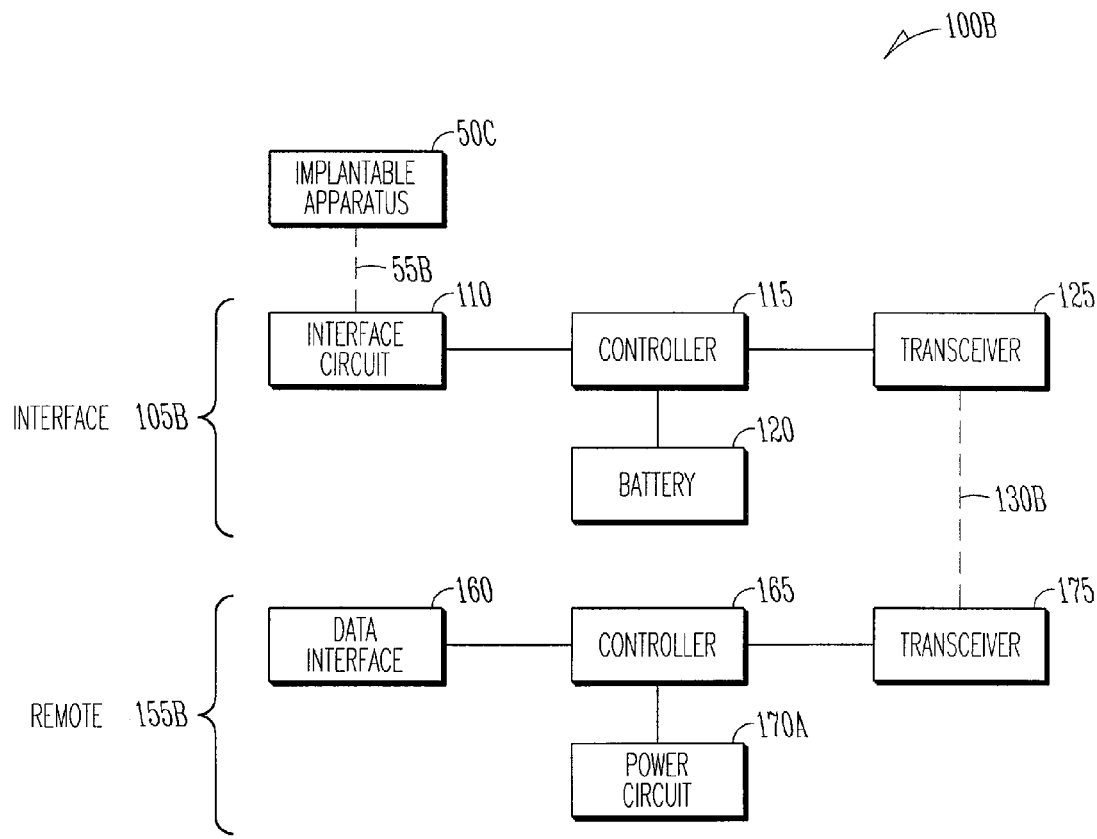

FIG. 1B illustrates an example of system 100B. System 100B includes implantable apparatus 50C, interface 105B and remote 155B. Implantable apparatus 50C is connected to interface 105B by link 55B. Link 55B, in various examples, includes a wired or wireless connection. In one example, implantable apparatus 50C includes a cardiac lead which is coupled to interface circuit 110 of interface 105B by a wired electrical connector. In one example, implantable apparatus 50C includes an implantable device having a near field or far field telemetry system and link 55B represents a wireless connection.

Interface 105B includes interface circuit 110, controller 115, transceiver 125 and battery 120. Interface circuit 110, in various examples, includes a circuit for establishing a coupling with implantable apparatus 50C. In various examples, interface circuit 110 includes a wireless receiver, transmitter or transceiver.

Interface circuit 110 is coupled to controller 115 by a wired connection. Controller 115, in various examples, includes analog or digital circuitry to allow communication between implantable apparatus 50C and remote 155B. In one example, controller 115 includes a processor and memory having instructions stored thereon to allow bi-directional communication of analog and digital data.

Controller 115 is coupled to battery 120 by a wired connection. Battery 120, in various examples, includes a power supply that is isolated from a metered line service. Battery 120, in various examples, include a non-rechargeable battery or a rechargeable battery. Battery 120, in various examples, provides power for interface circuit 110, controller 115, transceiver 125 or other circuitry. In one example, battery 120 provides power for analyzing implantable apparatus 50C. In one example, battery 120 includes circuitry to provide a charging current to a rechargeable electrical power source. Controller 115 exchanges data or information with interface circuit 110.

Transceiver 125 is coupled to controller 115 by a wired connection. Transceiver 125 is denoted as including a transmitter as well as a receiver, however, in various embodiments, transceiver 125 includes a discrete transmitter or receiver. Transceiver 125 exchanges data or information with controller 115 and allows wireless communication with remote 155B.

Remote 155B includes, in one example, data interface 160, controller 165, transceiver 175 and power circuit 170A. Remote 155B exchanges data with a communication network or provides and receives user-accessible data.

Transceiver 175 is coupled to controller 165 by a wired connection. Transceiver 175 is denoted as including a transmitter as well as a receiver, however, in various embodiments, transceiver 175 includes a discrete transmitter or receiver. Transceiver 175 exchanges data or information with controller 165 and allows wireless communication with implantable apparatus 50C via link 130B.

Controller 165, in various examples, includes analog or digital circuitry to allow communication between implantable apparatus 50C and remote 155B. In one example, controller 165 includes a processor and memory having instructions stored thereon to allow bi-directional communication of analog and digital data. Controller 165 exchanges data or information with implantable apparatus 50C.

Controller 165 is coupled to power circuit 170A by a wired connection. Power circuit 170A, in various examples, includes a power supply that is isolated from a metered line service. In various examples, power circuit 170A includes a non-rechargeable battery or a rechargeable battery. Power circuit 170A, in various examples, provides power to controller 165, data interface 160, transceiver 175 or other circuitry. In one example, power circuit 170A provides power for evaluating implantable apparatus 50C. Controller 165 exchanges data or information with data interface 160.

Data interface 160, in various examples, includes an interface to allow connecting remote 155B with a bi-directional communication network such as a local area network, a wide area network or a telephone line (not shown). In various examples, data interface 160 includes a display monitor, a printer, a keyboard, a touch-sensitive screen, a cursor control, a speaker, a microphone, a storage device and a network interface device.

Figure 2:
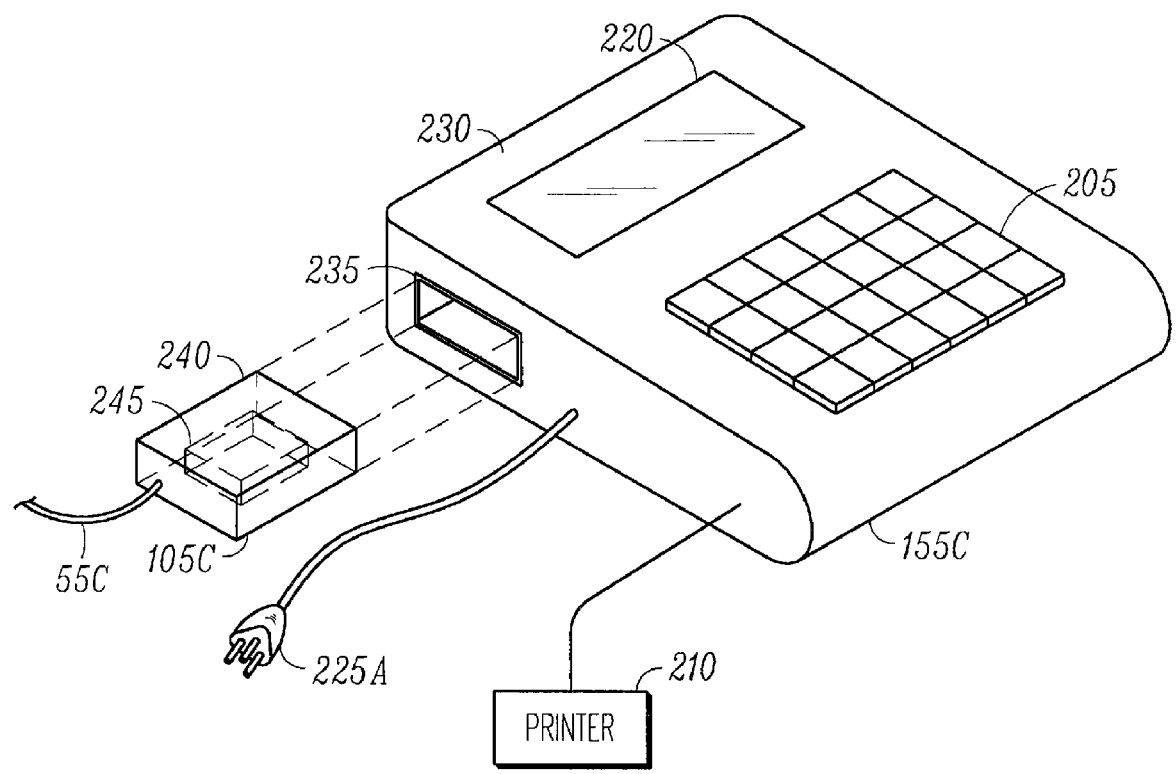
FIG. 2 includes an illustration of an interface device and a remote programmer.

FIG. 2 illustrates a view of interface 105C and remote 155C. Interface 105C includes housing 240 and coupler 245. Link 55C represents a wired connection between interface 105C and an implantable apparatus (not shown).

Coupler 245, in various examples, includes a wireless device (such as a magnetic device, an optical device or an acoustical device) or a wired electrical connector. Coupler 245 provides data communication on link 130B between an implantable apparatus and remote 155C and in one example, coupler 245 also provides electrical isolation. A magnetic device provides data communication and isolation using modulated magnetic signals. An optical device provides data communication and isolation using modulated light. An acoustical device provides data communication and isolation using modulated acoustical signals. A wired connection provides data communication using modulated electrical levels. In one example, coupler 245 includes one or more electrical contacts that are protected or otherwise guarded in a manner to reduce the risk of dangerous electrical levels to a patient.

In one example, coupler 245 is connected to battery 120 and conveys power from remote 155C to interface 105C for battery charging. Housing 240, in various examples, provides a containment structure for at least one of any combination of interface circuit 110, controller 115, battery 120 and transceiver 125. In various examples, housing 240 is fabricated of plastic, metal or other materials including conductive and non-conductive materials.

Remote 155C includes housing 230, display 220 and keyboard 205. Remote 155C is powered by a connection to a metered line service via electrical connector 225A. In one example, power circuit 170A includes electrical connector 225A and a medical grade isolated power supply. Power circuit 170A, in one example, includes an isolation transformer and other circuitry. Power circuit 170A provides isolation to prevent electrical signals appearing on the metered line service from appearing at implantable apparatus 50C.

In various examples, housing 230 is fabricated of plastic, metal or other materials including conductive and non-conductive materials. Housing 230 provides containment for at least one of any combination of data interface 160, controller 165, power circuit 170A and transceiver 175.

Display 220 provides a visual display for data. The data, in various examples, corresponds to a communication session, device identification or data entered by means of keyboard 205. Keyboard 205 is illustrated as a multi-key keyboard, however other data entry devices are also contemplated, including, for example, a mouse, trackball, touch-sensitive screen or other devices.

In FIG. 2, remote 155C is coupled to printer 210. Printer 210 provides a printed version of data available at remote 155C. Other external or internal peripheral devices are also contemplated for remote 155C, including, for example, a memory or storage device, a network interface and an audio transducer such as a microphone or speaker.

In one example, housing 230 includes a feature tailored to mate with housing 240. In FIG. 2, housing 230 includes receiver 235 having dimensions and a configuration to mate with and receive housing 240. Housing 230 serves as a docking station for interface 105C. When interface 105C is docked to remote 155C, coupler 245 is aligned to allow communication using link 130B. In one example, coupler 245 includes an electrical connection with corresponding electrical contacts on housing 230 (not visible in the figure) when docked. In one example, coupler 245 provides a connection whereby battery 120 can be recharged. Other features or configurations for mating housing 240 with housing 230 are also contemplated, including, for example, an alignment pin, slot or guide.

Figure 3A:
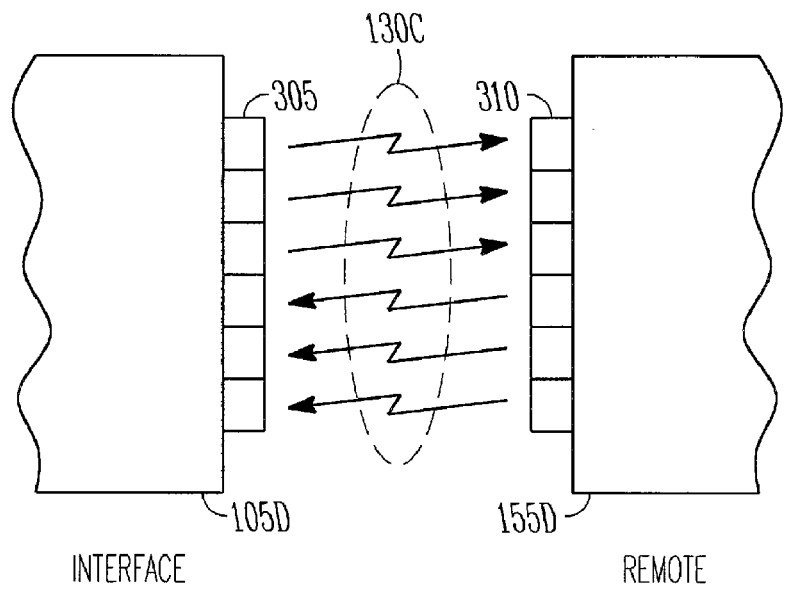
FIGS. 3A and 3B illustrate exemplary wireless transceivers.
Figure 3B:
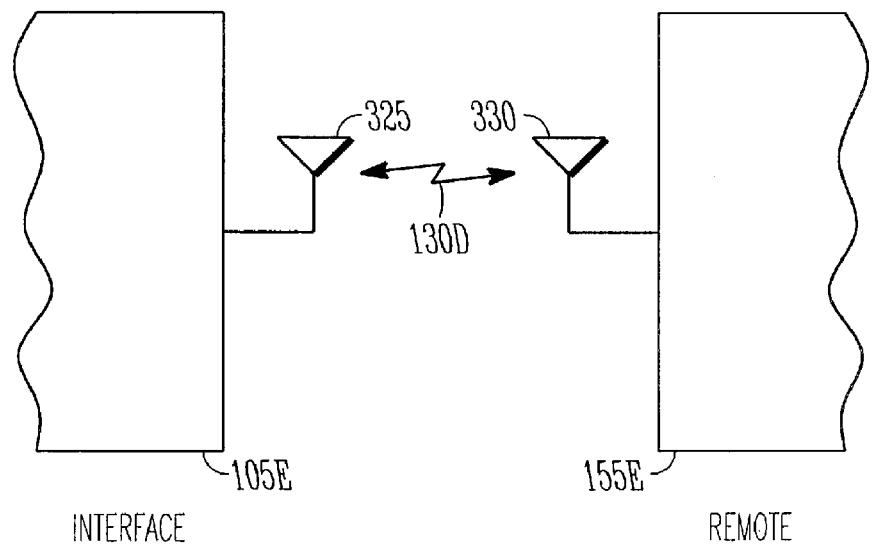

FIGS. 3A and 3B illustrate wireless link 130C and 130D, respectively. In FIG. 3A, interface 105D includes array 305 having six light emitting diodes and remote 155D includes array 310 of light emitting diodes or LEDs. In the figure, some of the light emitting diodes are configured to transmit and others are configured to receive optical signals. Other types of optical devices are also contemplated, including, for example, infrared light emitting diodes and laser devices. More or less than six individual optical elements are contemplated.

In FIG. 3B, interface 105E includes for field radio frequency (RF) antenna 325 in wireless communication with far field radio frequency antenna 330 of remote 155E.

Figure 4:
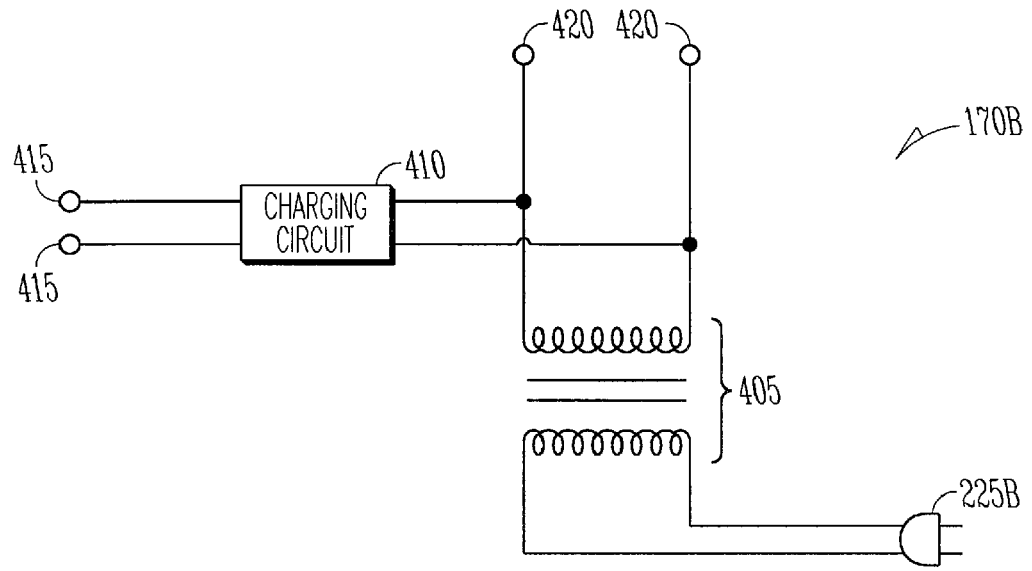
FIG. 4 illustrates a portion of a power circuit.

FIG. 4 illustrates one example of power circuit 170B. Electrical connector 225B is configured to provide power from a metered line service (not shown) and is connected to isolation transformer 405. Isolation transformer 405 is an iron core inductively coupled transformer, however, other types of isolation components or circuits are also contemplated. Transformer 405 is coupled to charging circuit 410 which includes circuitry for delivering a charging current to battery 120 using electrical contacts 415. In one example, contacts 415 are in communication with coupler 245 when interface 105C is docked with remote 155C. Transformer 405 is also coupled to nodes 420 which are connected, in one example, to controller 165 by a power supply circuit.

Figure 5:
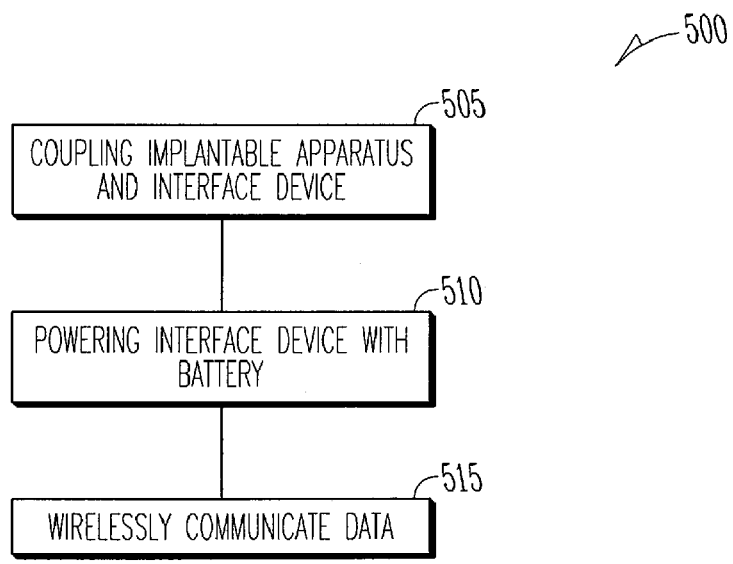
FIG. 5 illustrates a method for communicating.

FIG. 5 illustrates method 500 for communicating with an implantable device. At 505, implantable apparatus 50 is coupled to interface 105A by a wired or wireless link. At 510, interface 105A is powered by an electrical battery. At 515, data is wirelessly communicated between interface 105A and remote 155A. As such, data is sent to, and received from, implantable apparatus 50 using data interface 160 of remote 155B.

Exemplary Alternatives

In one example, interface 105A is connected by link 55A with a portion of an implantable apparatus. For example, an implantable electrical lead can be analyzed using the present system. Testing of an electrical lead may entail determining placement of an electrode tip, measuring impedance and checking mechanical or electrical integrity.

In one example, a mechanical connection is established between interface 105A and remote 155A. An electrical connection between interface 105A and remote 155A, in one example, is limited to a battery charging function. In one example, a lock-out circuit or device interrupts a battery charging current during an active communication session between implantable apparatus 50A and remote 155A.

In one example, link 130A includes a magnetic interface (or coupling), an inductive link, an acoustical link or an optical link. A low level magnetic coupling provides data communication and provides electrical isolation.

In addition to implantable apparatus 50A, other external devices can also be coupled to remote 155A using the present system. For example, a blood pressure cuff, a weight scale and other wireless modules can be configured to communicate with remote 155A via interface 105A.

In one example, interface circuit 110 is configured to connect with more than one implantable apparatus 50B or external device. For example, multiple leads of an implantable apparatus can be separately coupled to interface 105B and each such lead can be diagnosed and analyzed using remote 155B.

In one example, remote 155A executes a program sometimes referred to as a pacing system analyzer software application. The software application includes instructions for communicating with implantable apparatus 50A via interface 105A. In one example, data exchanged using the software application includes control information or instructions, test results and real-time data including markers and electrograms.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

What is claimed is:

1. An external interface device comprising:
   a first circuit to wirelessly communicate data with a wireless circuit of an external device;
   a controller coupled to the first circuit and configured to exchange data with the external device using the first circuit;
   a battery coupled to the controller;
   a second circuit coupled to the controller and adapted to couple with an implantable apparatus by a wired connection which is completely wired from the second circuit to the implantable apparatus, wherein the controller is configured to exchange electrical signals with the implantable apparatus using the second circuit; and
   wherein the first circuit, controller, battery, and second circuit are configured for use in a sterile field, and wherein the battery is electrically isolated from the external device.

2. The device of claim 1 wherein the first circuit includes an optical device.

3. The device of claim 2 wherein the optical device includes an infrared light emitting diode.

4. The device of claim 1 wherein the first circuit includes a far field radio frequency transceiver.

5. The device of claim 1 wherein the first circuit includes a magnetic interface.

6. The device of claim 1 wherein the second circuit includes a wireless transceiver.

7. The device of claim 1 wherein the battery includes a rechargeable battery.

8. The device of claim 1 further including a housing having at least one of the first circuit, the controller and the second circuit contained therein and the housing having a first feature configured to mate with a corresponding feature of the external device.

9. The device of claim 1 wherein the first circuit is configured to wirelessly communicate data beyond the sterile field.

10. The device of claim 1 wherein the second circuit is electrically isolated from a metered line service.

11. A system comprising:
 a first external device having an interface circuit configured to couple with an implantable apparatus by a wired connection which is completely wired from the interface circuit to the implantable apparatus, the first external device having a first controller coupled to the interface circuit, the first controller coupled to a battery and configured to exchange information with the implantable apparatus using a first transceiver coupled to the first controller;
 a second external device having a second transceiver adapted for wireless communication with the first transceiver, wherein the second external device includes a second controller coupled to the second transceiver and further including a data interface coupled to the second controller wherein the data interface is configured to at least one of receive data for communicating to the implantable apparatus and receive data from the second controller as a function of the information communicated from the implantable apparatus; and
 wherein the first external device is configured for use in a sterile field and wherein the battery is electrically isolated from a metered line service.

12. The system of claim 11 further including a power circuit coupled to the second controller wherein the power circuit includes a connector for coupling with the metered line service.

13. The system of claim 12 wherein the power circuit includes an isolation component.

14. The system of claim 13 wherein the isolation component includes an isolation transformer.

15. The system of claim 12 wherein the power circuit includes a charging circuit to provide a current to the battery.

16. The system of claim 11 wherein the implantable apparatus includes at least one of a therapy circuit, a monitor circuit, an electrode and a lead.

17. The system of claim 11 wherein the first transceiver includes at least one of a far field radio frequency transceiver, a magnetic interface and an optical device.

18. The system of claim 17 wherein the optical device includes an infrared light emitting diode.

19. The system of claim 11 further including:
 a first housing having at least one of the interface circuit, the first transceiver and the first controller contained therein, wherein the first housing includes a first feature; and
 a second housing having at least one of the second transceiver, the data interface and the second controller contained therein; wherein the second housing includes a second feature; and
 wherein the first feature is configured to mate with the second feature.

20. The system of claim 19 wherein the first housing includes electrical contacts for coupling to the battery.

21. The system of claim 11 wherein the data interface includes at least one of a display screen, a touch-sensitive display, a keyboard, a removable storage device, a third wireless transceiver and a network interface circuit.

22. A method comprising:
 establishing a wired connection between a first electrical circuit of an implantable apparatus and a first external device wherein the wired connection is completely wired from the first electrical circuit to the first external device, the first external device including a non-implantable housing and configured for use in a sterile field;
 powering a controller of the first external device with a battery; and
 wirelessly communicating data between the first external device and a second external device, the second external device having a power supply electrically isolated from the battery.

23. The method of claim 22 wherein wirelessly communicating includes communicating using a far field radio frequency signal.

24. The method of claim 22 wherein the second external device includes a programmer housing and further including mating a first feature of the non-implantable housing with a second feature of the programmer housing.

* * * * *